United States Patent
Catania et al.

(10) Patent No.: US 7,731,365 B2
(45) Date of Patent: Jun. 8, 2010

(54) METHOD OF FITTING CONTACT LENSES

(75) Inventors: Louis J. Catania, Atlantic Beach, FL (US); Edgar V. Menezes, Jacksonville, FL (US)

(73) Assignee: Johnson&Johnson Vision Care, Inc., Jacksonville, FL (US)

( * ) Notice: Subject to any disclaimer, the term of this patent is extended or adjusted under 35 U.S.C. 154(b) by 156 days.

(21) Appl. No.: 12/050,533

(22) Filed: Mar. 18, 2008

(65) Prior Publication Data

US 2008/0231810 A1   Sep. 25, 2008

(51) Int. Cl.
*A61B 3/00*   (2006.01)
*A61B 3/10*   (2006.01)

(52) U.S. Cl. .................. 351/247; 351/212; 351/219

(58) Field of Classification Search .......... 351/205–247
See application file for complete search history.

(56) References Cited

U.S. PATENT DOCUMENTS

| 3,781,096 | A  | * | 12/1973 | Townsley | 351/212 |
|---|---|---|---|---|---|
| 4,598,984 | A  | * | 7/1986 | Rol | 351/219 |
| 5,293,533 | A  | * | 3/1994 | Klyce | 351/247 |
| 6,511,180 | B2 |   | 1/2003 | Guirao et al. | 351/211 |
| 6,688,745 | B2 |   | 2/2004 | Ross et al. | 351/205 |
| 6,997,555 | B2 |   | 2/2006 | Dick et al. | 351/211 |
| 7,360,892 | B2 | * | 4/2008 | Tung | 351/177 |
| 2004/0263786 | A1 | | 12/2004 | Williams et al. | 351/246 |
| 2005/0200809 | A1 | | 9/2005 | Dreher et al. | 351/246 |

* cited by examiner

*Primary Examiner*—Mohammed Hasan
(74) *Attorney, Agent, or Firm*—Todd F. Volyn

(57) ABSTRACT

The invention provides a method of fitting lenses that results in correction of not only low and high order ocular aberrations, but that additionally provides correction for the effects of cortical influences, or neuro-adaptive influences.

7 Claims, 1 Drawing Sheet

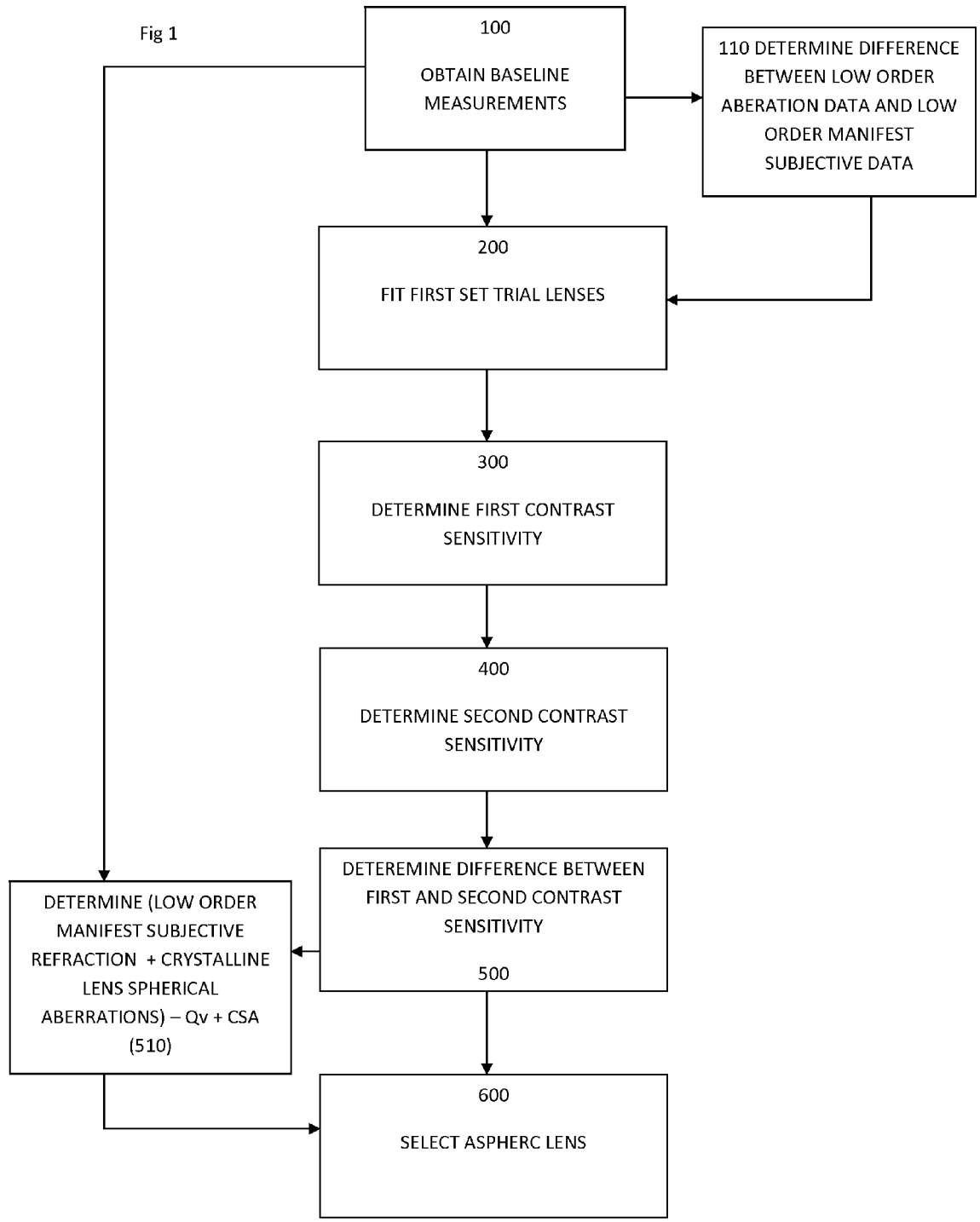

METHOD OF FITTING CONTACT LENSES

FIELD OF THE INVENTION

The invention relates to the fitting of contact lenses. In particular, the invention provides a method of fitting contact lenses that corrects for the individual's lower order aberrations and substantially all of the spherical aberrations as well as correcting for the neuro-adaptive effects on vision.

BACKGROUND OF THE INVENTION

Correction of refractive errors using contact lenses is well known. Conventional contact lenses provide correction for low order optical aberrations, such as defocus and astigmatism, leaving higher order aberrations uncorrected. Recently, contact lenses for correction of higher order aberrations, such as third order coma and spherical aberrations, and irregular astigmatism have been disclosed as well. These lenses are disadvantageous in that their design and fitting does not take into account both the cortical influences, meaning the neuro-adaptive influences of the individual's visual cortex on vision, and the changes associated with spherical aberrations, particularly those spherical aberration changes associated with aging. Thus, the known corrections for spherical aberration and other high order aberrations have been problematic because of the multiple variables and optical challenges associated with correcting these aberrations in humans.

For example, one such type of correction, aspheric contact lenses, are known to reduce by as much as 40 to 60% of spherical aberrations, which are the most common and disabling of the high order aberrations for human vision. The reason that not a greater percentage of spherical aberrations are corrected by aspheric contact lenses is that the conventional aspheric contact lenses and methods of fitting such lenses address only lower order visual acuity, or the quantitative vision of an individual. This ignores neuro-adaptive effects.

BRIEF DESCRIPTION OF THE DRAWINGS

FIG. 1 is a flow chart of the method of the invention.

DETAILED DESCRIPTION OF THE INVENTION AND PREFERRED EMBODIMENTS

The invention provides a method of fitting lenses that results in correction of not only low and high order ocular aberrations, but that additionally provides correction for the effects of cortical influences, or neuro-adaptive influences. In a preferred embodiment, the method provides correction for the chronological aging changes in vision. An advantage of the method of the invention is that the final fitted lens will correct for substantially all of the lens wearer's spherical aberrations.

In the first step of the method of the invention, certain baseline measurements are obtained from an individual. The minimum data obtained in this baseline measurement step are: low order aberration data; low order manifest subjective data; high order aberrations resulting from the crystalline lens; corneal data; and individual visual requirements. Preferably, the baseline measurements also include slit lamp evaluation of the cornea; individual visual acuity history; tear film volume, chemistry and quality analysis; pinhole acuity; and near point analysis.

The low order aberration data are measurements of the individual's monocular distance sphere and cylinder correction using conventionally available equipment such as an autorefractor, a phoropter, or a wavefront aberrometer. Additionally, the low order manifest subjective data, meaning the monocular distance subjective visual performance of the individual to a given sphere or cylinder correction, is obtained by any convenient means including, without limitation, the use of Snellen charts.

The high order aberration crystalline lens data, meaning the high order aberrations resulting from the crystalline lens, will be at least third and higher order spherical aberrations and preferably will be at least fourth and higher order spherical aberrations, and more preferably fourth order spherical aberrations. The measurements may be carried out by any conventional wavefront aberrometry method that is capable of determining the aberrations attributable to the total eye, the crystalline lens, and the cornea. Suitable apparatuses for performing the measurements are commercially available from, for example, Marco Ophthalmics, Jacksonville, Fla.

The high order aberrations, generally, are any departure from a spherical wavefront, after subtracting out the low order aberrations such as sphere and cylinder, at any position on the wavefront and may be represented by mathematical descriptors including, without limitation, Zernike polynomials, surface fitting functions including, without limitation, Taylor series polynomials, Seidel coefficients and the like. Preferably, Zernike polynomials are used in the method of the invention.

For purposes of the invention, it is preferred that the low and high order aberration measurements be performed with the pupil at a fixed diameter. The precise diameter at which to make the measurements may be determined by a consideration of the individual's daily tasks and adjusted for the chronological aging examination process. For example, if the individual spends much of the day in performing tasks in lowlight, mesopic or scotopic, situations, the measurements preferably are made with a substantially fully dilated pupil. However, this may change from year-to-year with changes in the individual's vocational or avocational pursuits and physiological pupil changes. Preferably, the pupil of the individual is measured at a selected luminance to determine the diameter to be used.

Corneal data is obtained based on corneal topographic evaluation of the radius and curvature of the cornea at a center, or apical, point and at a peripheral point of the cornea. The peripheral point preferably is at about 70% of the pupil diameter.

The individual visual requirement measurements may be gathered by any known method and the data gathered will include, without limitation corrected and uncorrected distance and near visual acuities. Optionally, the visual history may be obtained, which will include a careful interview of the individual regarding vocational and avocational visual needs and desires.

Also optionally, tear film, pinhole acuity, and near point analysis data is obtained. Tear film volume may be obtained, for example, using Schirmer's test and the chemistry and volume of the tear fluid is analyzed by known methods for tear chemistry and viscosity. Pinhole visual acuity may be assessed using a pinhole disc. Finally, a near point analysis my be made of the amplitude of accommodation, meaning the distance over which an object may be moved toward the eye yet remain in focus, along with fusional, or convergence testing.

Once the baseline measurements are obtained, depending on the difference between the low order aberration data, the low order manifest subjective data, and the high order aberration data, the final aspheric lens may be selected or the individual's eye may be examined while wearing one or more trial lenses that are aspheric lenses. The asphericity may be on the front surface, the back surface, or both surfaces of the lens. For those individuals in which the difference between the low order aberration data and the low order manifest subjective refraction data is ≧about 0.50 diopters for the sphere or the sphere and cylinder power, or ≧about 10° in cylinder axis for cylinder power less than 2.00 diopters or ≧about 5° in cylinder axis for cylinder power greater than 2.00 diopters, then one or more trial fitting lenses are used as follows.

A first trial lens is selected based on the low order aberration data and the crystalline lens high order spherical aberrations less the corneal $Q_v$ measured for the individual. The $Q_v$ is the measure of the amount of spherical aberrations produced by the cornea measured as follows:

$$Q_v = \frac{(PCR)^2}{(CCR)^2}$$

wherein PCR is the peripheral corneal radius; and
CCR is the central corneal radius.

For purposes of this step of the method of the invention, the $Q_v$ measurement must be converted to root mean square ("RMS") units. Examples of formulae for carrying out this conversion are known as, for example, as described in U.S. Pat. No. 6,610,048 incorporated in its entirety herein by reference.

The first trial lens preferably is of a large diameter, meaning a diameter of greater than about 14 to 15 mm in diameter and is fit on the flattest K, meaning a K value that substantially neutralizes the effect of corneal asphericity variability. Alternatively, the lens back surface is a sphere or toric surface that substantially neutralizes the effect of corneal asphericity and astigmatism variability.

A first contrast sensitivity function measurement across all spatial frequencies is carried out of the first trial lens on-eye. Contrast sensitivity function testing may be carried out using any convenient method including, without limitation determining the lowest contrast at which a sinusoidal grating of a spatial frequency is detected and determining the reciprocal or calculating the product of the optical modulation transfer function and the neural contrast sensitivity function, Fourier analysis, and the like.

A second contrast sensitivity function measurement across all spatial frequencies is carried out, which measurement takes into account the difference between the low order aberrations data and the low order manifest subjective data. One method of carrying this step out is to make the contrast sensitivity function measurement while the individual has the first trial lens on eye and the eye is looking through a phoropter or trial frame into which the difference between the low order aberration data and low order manifest subjective data is inputted. Alternatively, a second trial lens is selected based on the measured low order manifest subjective refraction and the crystalline lens spherical aberrations less the corneal $Q_v$ and the second contrast sensitivity function measurement is carried out using the second trial lens.

The difference between the first and second contrast sensitivity measurements is then calculated. This difference is the cortical spherical aberration ("CSA"). The cortical spherical aberration will be in cycles/degree and, thus, the cortical spherical aberration must be converted to a wavefront, by any convenient method, for purposes of providing the final lens. Optionally and preferably, the CSA is also coverted to RMS units by any known method. By way of example, one such method is disclosed in Maeda, Patrick Y, "Zernike Polynomials and Their Use in describing the Wavefront Aberrations of the Human Eye," *Applied Vision and Imaging Systems Course Project*, Stanford (2003). If the CSA is <0.2 RMS, preferably the individual is not fitted with a final lens because the individual is unlikely to obtain a discernible benefit. The conversion of the CSA may be, and preferably is, customized to the individual's eye and indices of refraction according to the following equation:

$$CSA_{Cust} = CS_{Diff} \times \frac{SE}{SA}$$

wherein $CS_{diff}$ is the difference between the contrast sensitivity function measurement for the second lens and the first lens;
SE is the spherical equivalent of the individual's lower order manifest subjective refraction; and
SA is the spherical aberration of the individual's lower order refraction.

For those individuals in which the difference between the lower order aberration data and the lower order manifest subjective refraction data is <about 0.50 diopters for the sphere or the sphere and cylinder power, or <about 10° in cylinder axis for cylinder power less than 2.00 diopters or <about 5° in cylinder axis for cylinder power greater than 2.00 diopters or <0.4 total RMS, the trial fitting lens step may be omitted and the aspheric lens may be selected.

In the final step of the method of the invention, an aspheric lens is provided for the individual's eye. As for the trial lenses, the lens selected is of the largest diameter and is fit on the flattest K or as a back surface sphere or toric surface that substantially neutralizes the corneal asphericity and astigmatism variability. The lens selected is based on the measured low order manifest subjective refraction plus the crystalline lens spherical aberrations less the corneal $Q_v$ plus the CSA or $CSA_{Cust}$ or:

(low order manifest subjective refraction+crystalline lens spherical aberrations)–$Q_v$+CSA or (low order manifest subjective refraction+crystalline lens spherical aberrations)–$Q_v$+$CSA_{cust}$ FIG. 1 graphically shows the method of the invention. In step 100 baseline measurements art taken. These are used in steps 110 and 510 (together with data generated in step 500) to facilitate fitting the first trial lenses (step 200) and selecting aspheric lenses (step 600). After initial trial lenses are fitted, contrast sensitivity is determined in steps 300 and 400.

One ordinarily skilled in the art will recognize that the method of the invention may be tailored to fit spectacle lenses as well. In this embodiment, the $Q_v$ values are added, rather than subtracted, for total correction of the optical elements producing spherical aberrations. In an alternative embodiment, the invention may provide correction for binocular cortical processing through simultaneous use of the aforedescribed monocular method.

Although the method of the invention may be used at any point within an individuals' life, it may find its greatest utility if first carried out at about 19 years of age and at chronological intervals thereafter. After 19 years of age, it is believed that the individual's vision begins to deteriorate through induced spherical aberrations produced by a changing crystalline lens. Thus, initial measurements after 19 years of age will be less likely to obtain an optimal baseline for the individual. After the initial application, the individual is monitored, preferably every 6 months to 24 months depending on age, to determine if uncorrected changes in visual acuity are occurring.

What is claimed is:

1. A contact lens fitting method, comprising the steps of: a.) obtaining baseline measurements of low order aberration data; low order manifest subjective data; high order spherical aberrations resulting from the crystalline lens; corneal data; and visual requirements or an individual; b.) determining a difference between the lower order aberrations and the lower order manifest subjective refraction obtained in carrying out the baseline measurements in step a.); c.) fitting at least a first trial aspheric lens on an eye of the individual, wherein the first trial lens is selected based on the low order aberrations and the crystalline lens spherical aberrations less a corneal Qv; d.) carrying out a contrast sensitivity function measurement of the first trial lens; e.) obtaining a second contrast sensitivity function measurement that takes into account the difference between the low order aberration data and the low order manifest subjective data; f.) calculating the difference between the first and second contrast sensitivity function measurements; and g.) selecting an aspheric lens for the individual based on the following equation: (low order manifest subjective refraction+crystalline lens spherical aberrations)—

Qv+CSA wherein CSA is a cortical spherical aberration and using the selection to prescribe contact lenses that correct a patient's vision during wear.

2. The method of claim 1, wherein step e.) further comprises carrying out a second contrast sensitivity function measurement while the first trial lens is on eye and the individual is viewing through a phoropter or a trial frame into which the difference between the low order aberration data and low order manifest subjective refraction data is inputted.

3. The method of claim 1, wherein step e.) further comprises (i) fitting a second trial aspheric lens on the eye of the individual, wherein the second trial lens is selected based on the low order manifest subjective data and the crystalline lens spherical aberrations less a corneal Qv and (ii) carrying out a second contrast sensitivity function measurement using the second trial lens.

4. The method of claim 1, wherein step a.) further comprises obtaining measurements of a slit lamp evaluation of the cornea, an individual visual acuity history, a tear film volume, chemistry and quality analysis; a pinhole acuity; and a near point analysis.

5. The method of claim 1, further comprising the step of repeating steps a) through g.) at chronological intervals during the individual's lifetime.

6. The method of claim 2, further comprising the step of repeating steps a) through g.) at chronological intervals during the individual's lifetime.

7. The method of claim 3, further comprising the step of repeating steps a) through g.) at chronological intervals during the individual's lifetime.

* * * * *